United States Patent [19]

MacDonald et al.

[11] 4,145,714
[45] Mar. 20, 1979

[54] TELEVISION FLAW DETECTOR FOR INSPECTING THE WALL SURFACE OF A HOLE THROUGH A CIRCUIT BOARD

[75] Inventors: Robert W. MacDonald, San Fernando; Robert W. Yates, Woodland Hills, both of Calif.

[73] Assignee: Robert W. MacDonald, San Fernando, Calif.

[21] Appl. No.: 881,652

[22] Filed: Feb. 27, 1978

[51] Int. Cl.² .................... H04N 7/18; G01N 21/32; G02B 21/10
[52] U.S. Cl. .................................. 358/106; 350/89; 356/241
[58] Field of Search ....................... 358/101, 106, 107; 356/241, 237; 350/89

[56] References Cited

U.S. PATENT DOCUMENTS

| | | | |
|---|---|---|---|
| 3,647,961 | 3/1972 | Blitchington | 358/106 |
| 3,661,440 | 5/1972 | Takahashi | 356/241 |
| 3,873,211 | 3/1975 | Watson | 356/241 |
| 3,920,311 | 11/1975 | Tsuda | 350/89 |
| 3,922,097 | 11/1975 | Nachet | 356/241 |
| 3,983,388 | 9/1976 | Gugliotta | 356/241 |
| 4,028,728 | 6/1977 | Sharp | 358/106 |

*Primary Examiner*—Howard W. Britton
*Attorney, Agent, or Firm*—Fulwider, Patton, Rieber, Lee & Utecht

[57] ABSTRACT

A television flaw detector, and process, for inspection of the wall surface of a hole through a circuit board. The circuit board is positioned on a support beneath a microscope, with the hole to be inspected aligned with the microscope. On the opposite side of the circuit board are an optical condenser and a light source. The condenser directs a divergent conical beam of light into the hole to illuminate the wall surface of the hole about its entire circumference and along its full length. A mask prevents non-reflected light rays from passing directly through the condenser and the hole into the microscope. A television camera mounted on the microscope is connected to a television monitor upon which it produces an image of a region of the wall surface of the hole extending from its full circumference at a selected position along its length.

8 Claims, 5 Drawing Figures

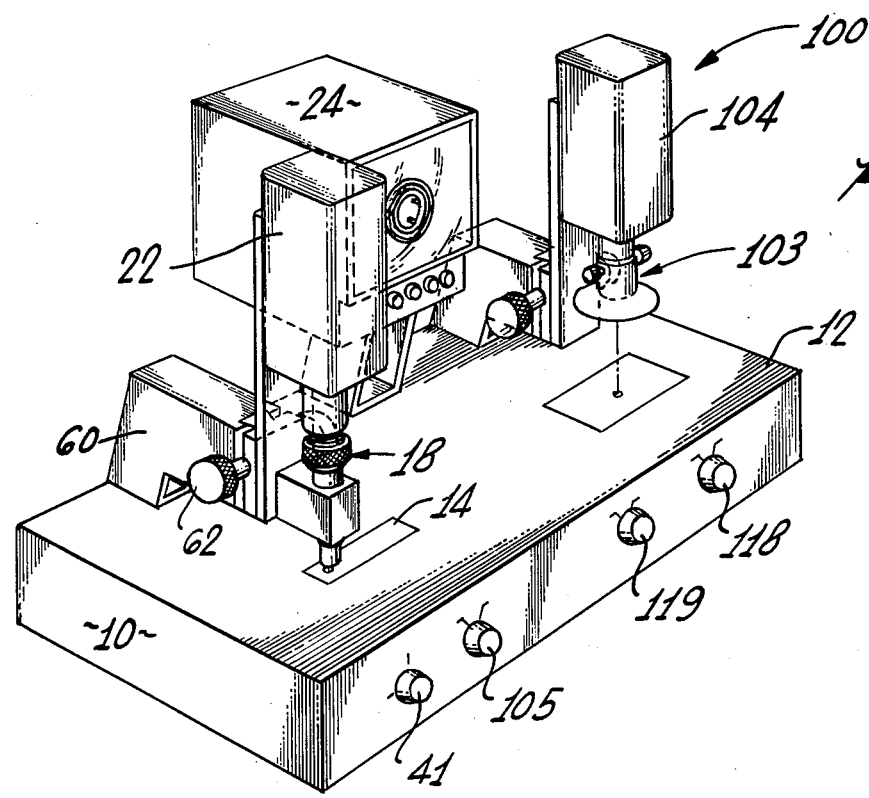
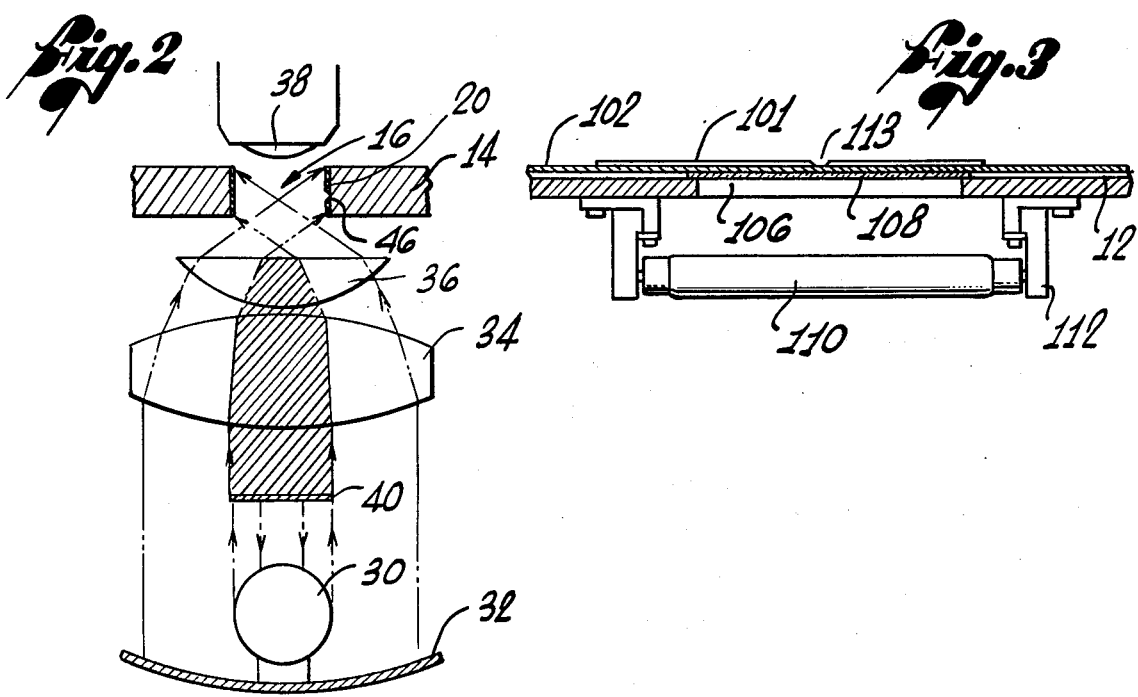

TELEVISION FLAW DETECTOR FOR INSPECTING THE WALL SURFACE OF A HOLE THROUGH A CIRCUIT BOARD

BACKGROUND OF THE INVENTION

This invention relates to a television flaw detector and process for inspecting the wall surface of a hole through a printed circuit board.

In the manufacture of a printed circuit board it is commonly necessary for holes to be drilled through the circuit board and subsequently plated along their wall surface with a conductive material to provide a circuit connection from one side of the circuit board to the other. Problems preventing the creation of an electrically conductive path through the hole can arise in the drilling of the hole or in the plating of the conductive material. The problems that can arise in drilling are associated with the composition of the board itself. Most circuit boards are made of one or more layers of fiberglass cloth impregnated with resin. If the board is drilled too fast, or is drilled with a drill which is not sufficiently sharp, the fibers are not severed flush with the wall surface of the hole but can project as whiskers which inhibit the continuity of deposition of conductive material on the wall surface. Accordingly, it is customary to examine the holes being drilled in sample boards and, if the wall surface is unsatisfactory, to alter the drill speed or change to sharper drills, as necessary, until a smooth wall surface is obtained. Even if the holes are adequately drilled, the deposition of material during plating may sometimes be defective and it is necessary to examine the wall surface of plated samples to see that ring voids, pits and other discontinuities in the plating are not present which would open circuit, or otherwise impair, the electrical path through the hole.

Inspecting the wall surface of holes through a circuit board has commonly been done by observing the holes from the top through a magnifying lens held over the circuit board, with the board resting on an underlying illuminated surface such as a frosted glass lighting table or the like. Such a method does not provide an adequately detailed view of the interior of the wall surface due to insufficiency and unevenness of the relatively small proportion of the light reflected from the wall surface and its tendency to be blinded out by the relatively greater intensity of the light passing directly through the hole. The image produced by such a lens is also subject to optical distortion at the outer region of the lens, and such inspection is both tedious and unreliable.

Another inspection technique involves the use of a conventional optical microscope but this also has significant problems. Using a microscope mirror or conventional bright field condenser to direct light upwardly through the hole into the microscope results in directing the bulk of the light rays directly through the hole without reflection off its wall surface into the microscope. Whatever scattered light rays may have reflected off the wall surface of the hole are relatively blinded out by the relatively greater intensity of the light rays which pass directly from the light source into the eye piece. As a result, the wall surface may be inadequately illuminated, without sufficient contrast or detail, to enable defects to be detected. Further, for inspection of circuit boards being produced on a production line basis, the use of a microscope which requires its operator to peer all day through an eye piece is tedious, creates eyestrain and is not conducive to prolonged high productivity.

A previous approach to the inspection of printed circuit boards for defects, intended to obviate the tediousness and eyestrain associated with using an ordinary magnifying lens, has utilized a television camera to view the surface of the printed circuit board and produce an enlarged image thereof on a television monitor, as disclosed in U.S. Pat. No. 4,028,728, issued to Benny H. Sharp on June 7, 1977. Such prior device is used to examine the soldered fillets connecting circuit paths on a printed circuit board, utilizing polarized light directed in a path parallel to the surface of the circuit board and impinging upon the tops of the fillets to produce spots of a different intensity of illumination as displayed on the monitor. Such prior device was not, however, addressed to the problem of examining the wall surfaces of holes through the circuit board and contains no provision for directing illumination into such holes to illuminate their wall surface for viewing by the television camera.

In the field of microscopy generally, it has been known to utilize so-called "dark-field" or "dark-ground" condensers to direct light rays obliquely to reveal the presence of small particles by scattering of light rays against a dark background while blocking off passage of light directly from the condenser into the microscope. Devices of that type are shown in U.S. Pat. Nos. 2,415,732, issued to E. Domingo on Feb. 11, 1947; 3,161,717, issued to Barabas et al. on Dec. 15, 1964 and 3,920,311, issued to Tsuda et al. on Nov. 18, 1975. Such prior devices were not, however, adopted to meeting the special circumstances which arise in examining the wall surface of a hole.

SUMMARY OF THE INVENTION

This invention provides a television flaw detector in which light is directed into one side of the hole in a circuit board in a manner which provides uniform illumination over the wall surface of the hole along its entire length and about its entire circumference for viewing by a microscope positioned on the opposite side of the hole. The image produced by the microscope is viewed by a television camera connected to a television monitor which displays an image of a region of the wall surface extending about the complete circumference of the hole at a selected position along its length. The region selected for inspection can be varied selectively from one end of the hole to the other so that a complete inspection of the hole may be performed.

By utilizing the invention, a manufacturer of circuit boards can inspect the quality of holes drilled in the circuit board for the entire length of each hole to detect the presence of fiber whiskers projecting into the hole or other wall surface defect. The invention can also be used, after the holes have been plated, to examine the quality and integrity of the plating over the entire wall surface in order to detect imperfections, such as ring voids or pits, which could result in an open circuit or otherwise defective electrical path through the hole.

The lighting for the hole is provided by a light source and an optical condenser positioned between the hole and the source. The condenser shapes the light rays from the source into a divergent conical light beam aligned with the hole in the circuit board entering it on its side remote from the microscope. The conical light beam illuminates the wall surface of the hole about its circumference and along its full length. To avoid the light reflected from the wall surface being relatively blinded out by passage of non-reflected light from the light source directly through the condenser and the hole into the microscope, a mask is positioned between the light source and the condenser. The size and position of the mask is controlled to prevent light from passing directly through the hole. By adjusting the intensity of the light source, it can be arranged that the intensity of the reflected light is ample to meet the threshold light intensity requirements for the television camera. The foregoing features ensure that an adequately, detailed and bright image is displayed upon the television monitor.

To enable the hole to be progressively inspected at different regions along its entire length, the microscope is mounted for axial movement toward and away from the hole so that the axial position of the region viewed can be varied between the top and bottom of the hole. The microscope includes a focusing mechanism so that, at each selected region of inspection, the image produced by the microscope can be refocused to produce a sharp image to be viewed by the television camera in order to ensure that a sharply focused image is displayed upon the television monitor.

The foregoing, and other aspects of the invention are set forth more fully in the detailed description hereafter.

BRIEF DESCRIPTION OF THE DRAWINGS

A television flaw detector constructed in accordance with the preferred embodiment of the invention is illustrated in the accompanying drawings in which:

FIG. 1 is a perspective view of a circuit board inspection apparatus incorporating, on the left side thereof, a television flaw detector constructed according to the invention.

FIG. 2 is a cross-sectional, side view of an optical condenser forming a part of the television flaw detector shown in FIG. 1;

FIG. 3 is a cross-sectional end view of part of a lighting table forming a part of a surface inspection unit forming a part of the circuit board inspection apparatus shown in FIG. 1;

DETAILED DESCRIPTION

Figures 4, 5:
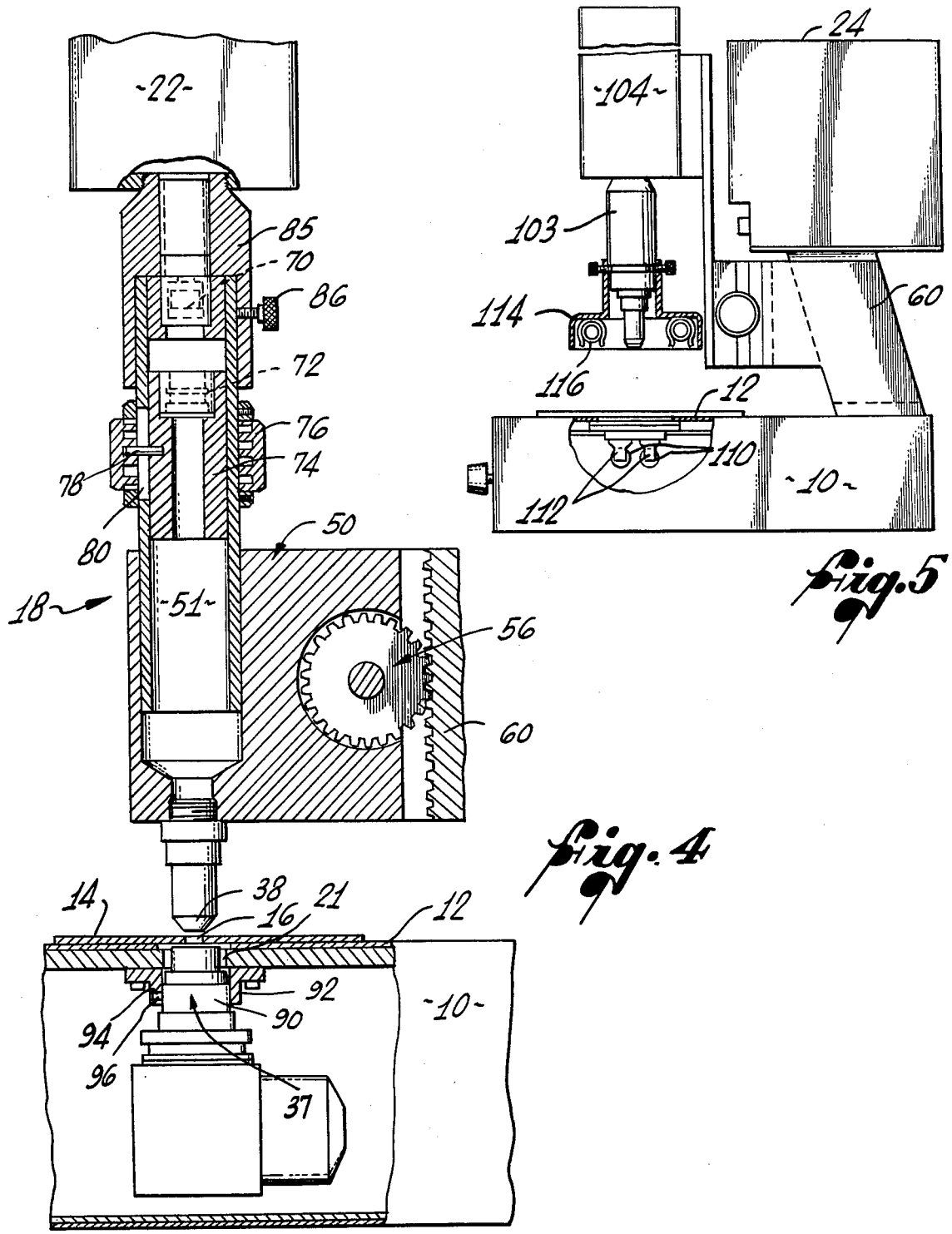
FIG. 4 is a cross-sectional side view of the television flaw detector shown in FIG. 1.
FIG. 5 is a side view of the surface inspection unit shown in FIG. 3.

A television flaw detector constructed in accordance with the preferred embodiment of the invention is illustrated in FIGS. 1 and 4 of the drawings. It includes a rectangular housing 10 having a flat horizontal upper wall 12 constituting a support for a circuit board 14 being subjected to examination. The circuit board 14 has at least one hole 16 through it which is aligned with the optical axis of a microscope 18 mounted on the support and spaced above the circuit board. The microscope views the wall surface 20 (FIG. 2) of the hole by light rays reflected from the wall surface and incident upon it from beneath through an opening 21 in the housing. The image produced by the microscope is viewed by a television camera 22 which is electrically connected to a television monitor 24 to display an image 26 of a region of the wall surface extending about its entire circumference at a selected position along the hole. The microscope may be adjusted vertically and focussed to select different regions along the length of the hole for examination so that the wall surface may be examined over its entire length.

A particularly significant aspect of the invention is the arrangement by which light rays are directed into the hole and reflected off the wall surface into the microscope, as shown in FIG. 2. Light rays are emitted from a light source comprising a light bulb 30 mounted in front of a conventional reflector 32. The light rays from the reflector are reflected towards an optical condenser comprising a double convex lens 34 and a plano-convex lens 36. A condenser housing 37 (FIG. 4) supports the lenses 34 and 36, the light source and the reflector 32 with their optical axes in alignment with the optical axis of the microscope. The hole 16 in the circuit board is positioned in axial alignment with the common optical axis of the foregoing optical elements.

The focal lengths of the lens 34 and 36 and their positioning in relation to the objective lens 38 of the microscope are such that a generally conical beam of light is directed from the condenser towards the objective lens but at a sufficiently divergent angle to exclude light from passing directly into the objective lens. This result is achieved by arranging the condenser lenses 34 and 36 to have a combined numerical aperture of about 0.9 while the objective lens 38 of the microscope has a numerical aperature typically in the range of 0.2 to 0.6. The term numerical aperture refers to the most diverse angle of light leaving the condenser lenses, or to the most diverse angle of light entering the objective. In mathematical terms it is the sine of the half angle formed from the focal point to the lens itself. In addition, the planar surface of the lens 36 is positioned so close to the underside of the circuit board that the focal point of the combined condenser lenses is positioned axially within, or outside but close to the entrance of, the hole. Actually, the condenser lenses do not focus all the rays at exactly the same focal point but the rays converge towards and pass through a focal point region before diverging, which region has a finite axial length which is comparable to the thickness of a typical circuit board, for example, about 60 thousandths of an inch. With this arrangement, the conical beam of light illuminates the wall surface of the hole uniformly about its entire internal circumference and for its full axial length. Without such uniform lighting along the length of the hole, poorly illuminated regions of a satisfactory quality might misleadingly resemble defects upon the monitor screen or actual defects within poorly lit regions of the hole might not be visible.

In order that the microscope should view the wall surface of the hole only by light reflected from it, light rays in the central region of the condenser, which would otherwise pass centrally through the condenser lenses and the hole into the microscope objective are blocked off by a mask 40 (FIG. 2). The mask is positioned on the incident side of the double convex lens 34 spaced co-axially therefrom. The diameter of the disk 40 is determined by selecting what is the largest hole diameter in the circuit board that the apparatus will be used to inspect (60 thousandths of an inch diameter in the preferred embodiment, although other figures could be selected) and then determining empirically what diameter of the mask is just large enough to prevent light rays from the source from passing directly through the lenses into the microscope objective lens without reflection from the wall surface of the hole.

The inspection of a hole wherein the wall surface 20 is constituted by a plating having a pitted region 46, is illustrated in FIG. 2. The illumination provided by the conical beam of light impinging on the wall surface would clearly reveal the pitted region in the image appearing on the monitor screen.

To enable the intensity of illumination of the image produced by the microscope to be varied for the television camera, conventional electrical circuitry (not shown) including a brightness control knob 41 (FIG. 1) is provided for varying the electrical input to, and hence the brightness of, the light bulb 30. Thus, the intensity of lighting on the picture can be adjusted to the level desired by the operator for adequate picture contrast and detail on the television monitor.

The microscope 18 (FIG. 4) comprises a vertical hollow microscope body 50 defining an enclosed, vertical cylindrical chamber 51 extending along the optical axis of the microscope. The objective lens 38 is mounted at its lower end. The microscope body is connected by a conventional rack and pinion mechanism, generally designated as 56, to a vertical supporting column 60 mounted on the housing. A pair of spaced adjusting wheels 62 (FIG. 1) are connected to the opposite ends of a shaft (not shown) connected to the pinion portion of the rack and pinion mechanism, enabling the microscope to be traversed vertically along its optical axis to move the objective lens relatively toward and away from the hole 16 in the circuit board.

The image produced by the microscope appears at a microscope eyepiece 70 mounted at the opposite end of the housing 50. The eyepiece is a conventional microscope eyepiece assembly for producing a right image (i.e., right of the image corresponds to the right of the object viewed and top of the image corresponds to the top of the object viewed). To enable focusing of the image produced at the eyepiece, a focusing stage comprising a lens assembly 72 mounted within a tubular mount 74, is mounted within the microscope housing in optical alignment with the objective lens and the eyepiece. The lens assembly is mounted in a tubular mount 74 slidable axially within the microscope housing and can be adjusted by an internally threaded collar 76, rotably mounted around the exterior of the microscope body, which engages a pin 78 projecting from the mounting 74 through a slot 80. Rotation of the collar 76 moves the focusing lens assembly 72 toward or away from the objective, depending upon the direction of rotation of the collar 76, to produce a focused image at the eyepiece 70. In the preferred embodiment, the objective lens 38, the lenses in the focusing assembly 72 and the lenses in the microscope eyepiece 70 have a combined 40 times magnification. However, it will be appreciated that lenses resulting in a different combined power of magnification may be employed.

The image produced at the microscope eyepiece is viewed by the television camera 22 (FIG. 4) which is mounted on top of the microscope housing 50 by a slide-on tubular connection 85 and is frictionally secured by a securing screw 86. By releasing the screw 86 the television camera 22 can be slid upwardly off the microscope to enable the image to be viewed directly by the eye through the eyepiece if so desired. The television camera is of conventional construction and, in the preferred embodiment, is a model number WV 1000 closed circuit television camera maufactured by Panasonic Co., a division of Matsushita Electric, 1 Panasonic Way, Secaucus, N.Y. 07094. It will be appreciated that comparable closed circuit television cameras may be substituted.

The television camera 22 is electrically connected to the previously mentioned television monitor 24 to produce the magnified, right image 26 on the monitor screen of the wall surface of the hole. In the preferred embodiment the television monitor is a model number WV 3000, 9 inch screen, closed circuit television monitor also manufactured by Panasonic Co. although other, comparable models may be used. The television camera and monitor have a combined magnification of ten times magnification relative to the image viewed. Thus, the total magnification of the image displayed on the screen in relation to the dimensions of the hole under inspection is 400 times in the preferred embodiment.

By displaying the image of the interior of the hole on a television monitor, the operator is spared the tedium and eyestrain of peering down the eyepiece of a microscope. Further, the use of the monitor enables several people to simultaneously view the interior surface of a hole to facilitate discussion when a problem arises, rather than requiring each of the participants to view the hole separately and in sequence.

In the inspection of a particular hole, a region along the length of the hole is selected for viewing and the focusing ring 76 is turned until a focused picture of the selected region of the hole extending 360° about the entire internal circumference thereof is displayed upon the television monitor. After that region has been inspected, the wheels 62 may be tuned to move the objective lens 38 axially relative to the hole to select a different axially spaced region of the hole for inspection, followed by refocusing and examination. In this way the hole may be inspected along its entire length for defects.

When setting up the instrument for examination of circuit boards of a particular thickness, an initial adjustment may be required of the vertical spacing between the optical condenser and the adjacent end of the hole to obtain generally uniform lighting of the hole along its axial length. To enable such vertical adjustment, the condenser housing 37 has a cylindrical region 90 forming a frictional sliding fit within a supporting ring 92 secured to the underside of the upper wall 12 of the housing. The frictional fit between the cylindrical portion 90 and the tube 92 allows relative sliding and axial motion between the two when force is applied by hand but with sufficient friction to resist movement of the condenser housing and its contents under the influence of its weight alone. A generally helical, closed slot 94 is provided in the wall of supporting ring 92 extending axially and circumferentially therein and receives a pin 96 fixedly secured to the condenser housing. The contacting edges of the slot 94 and the pin 96 function as a cam and cam follower upon application of twisting force by hand to the lens housing, guiding the lens system for relative axial motion towards and away from the circuit board depending upon the direction of twisting motion applied.

By this means, it is possible to selectively adjust the distance between the condenser and the hole in the circuit board. This adjustment can be made visually by watching the appearance of the image on the monitor until uniform illumination along the hole is achieved. Of course, for a run of circuit boards of the same thickness to be inspected, this adjustment will only need to be made at the start of the run and should not need to be altered for the remainder.

The invention also includes (FIG. 1) a second television flaw detector 100 for detecting discontinuities in a circuit board having opaque circuit elements 101 (FIG.

3), constituting metallic connection paths between circuit components, extending across a transparent or translucent substrate 102. The second flaw detector constitutes a microscope 103 and television camera 104 of the same construction as that previously described with respect to the first television flaw detector. The television camera 104 is also electrically connected to the television monitor 24 and, by suitable conventional electrical switching circuiting controlled by a switch 105 on the housing, the television monitor can display either the image transmitted by the camera 22 of the first flaw detector or the image from the camera 104 of the second flaw detector.

The second flaw detector can inspect the circuit board either by lighting from beneath the circuit board transmitted through the substrate or by reflected light directed downwardly onto the surface of the circuit board and reflected back up into the microscope lens. The two types of lighting are referred to, respectively, as back lighting and top lighting.

For back lighting, an opening 106 (FIG. 3) is provided in the support surface 12 of the housing in the region beneath the microscope 102. A light diffuser 108, such as a layer of frosted glass or translucent plastic, is connected to the support surface extending across the opening. The diffuser is illuminated from beneath by two straight, fluorescent lamps 110 mounted in conventional electrical fixtures 112 connected to the supporting structure. In use, the light provided by the fluorescent lamps illuminates the circuit board from beneath, highlighting any discontinuity, such as 113 (FIG. 3) in the circuit paths. Such discontinuities appear as brightly lit interruptions in the circuit elements, displayed on the television monitor.

Alternatively, top lighting may be used to illuminate the upper surface of the circuit board by reflected light. For this purpose, a circular, dished, downwardly facing, reflector 114 (FIG. 5) is secured to the lower end of the microscope 103. Mounted within the reflector 114, by conventional electrical lighting supports, is a toroidal fluorescent lamp 116. The light rays from the lamp 116 are directed downwardly by the reflector 114 onto the upper surface of the circuit board and reflected back upwardly into the microscope resulting in an image of the upper surface of the circuit board being displayed upon the television monitor. Conventional electrical circuitry provides for the brightness of the illumination of the back lighting provided by the lower fluorescent tubes 110 beneath the circuit board by a dimmer knob 118 and the top lighting provided by the upper fluorescent tube 116 by a dimmer knob 119.

Although the invention has been described with reference to the preferred embodiment, it will be appreciated that many changes and modifications within the competence of one of ordinary skill in this art may be made without departing from the spirit of the invention defined by the appended claims.

We claim:

1. In combination, a circuit board and a television flaw detector for inspecting the wall surface of a hole through the circuit board, the combination comprising,
    a support,
    a microscope connected to said support, said support supporting the circuit board with the hole axially aligned with the optical axis of the microscope, said microscope producing an image of a region of the wall surface extending around the complete circumference of the hole at a selected axial position therealong,
    a television camera connected to said microscrope for viewing the image produced thereby to produce electrical signals which will produce an image on a television monitor corresponding to the image produced by said microscope,
    a television monitor electrically connected to said television camera,
    a light source emitting light rays, connected to said support in spaced relation from the circuit board on an opposite side thereof from said microscope;
    optical condenser means connected to said support positioned between said light source and the circuit board in axial alignment with the hole therein for directing a divergent, generally conical beam of light into the hole to illuminate the wall surface of the hole about its entire circumference and throughout its axial length; and
    a mask connected to said condenser means for preventing light rays from said source not reflected from the wall surface of the hole from passing directly into the microscope.

2. A combination as defined in claim 1 wherein said microscope has an objective lens and wherein said condenser means causes the angle of divergence of the conical beam of light to be sufficient to direct the light rays onto the wall surface of the hole which can thereby be viewed by the objective lens.

3. A combination as defined in claim 2 wherein said condenser means comprises a combination of lenses wherein the combination has a numerical aperture of about 0.9 and wherein said objective lens has a numerical aperture in the range of about 0.2 to 0.6.

4. A combination defined in claim 2 wherein said condenser means comprises a combination of lenses wherein such lens combination on its emergent side has a focal length relatively shorter than the focal length of the objective lens and wherein the focal point of such lens combination is positioned within the axial length of the hole in the circuit board.

5. A combination as defined in claim 4 wherein the focal point of such lens combination constitutes a focal point region through which the light rays pass and thereafter diverge to form the conical beam, such focal point region being positioned within and generally axially co-extensive with the hole in the circuit board.

6. A combination as defined in claim 1 wherein said optical condenser means includes,
    a combination of lenses receiving rays of light on its incident side from said light source, said lens system on its emergent side directing the light rays through an initial region of convergence from which they diverge to form the generally conical beam; and
    a lens housing supporting the lens system away from the hole in the circuit board at a distance such that the light rays incident upon the wall surface are in the divergent portion of their paths.

7. A process for visually inspecting the wall surface of a hole through a circuit board utilizing a microscope, an optical condenser and a light source spaced successively along a common optical axis, a television camera for viewing an image produced by the microscope and a television monitor coupled to the television camera for displaying an image on the monitor corresponding to the image viewed by the video camera, the process comprising the steps of, positioning the circuit board between the microscope and the condenser with their optical axes aligned axially with the hole in the circuit board;

directing light rays from the light source by the condenser into a divergent, generally conical beam directed axially into the hole from the side thereof remote from the microscope to illuminate the wall surface of the hole about its entire circumference and throughout its axial length;

masking non-reflected light rays from passing directly through the condenser and the hole into the microscope, focusing the microscope upon a region of the wall surface extending around the complete circumference of the hole at a selected axial position therealong to produce an image thereof illustrated by reflected light only, viewing the image produced by the microscope with the television camera; and displaying an image of the selected region of the wall surface upon the television monitor.

8. A process as defined in claim 7 including an initial step of positioning the condenser in such spacing relative to the hole that a focal region of the condenser, through which the light rays which converge and thereafter diverge to form the conical beam, is positioned within the hole in the circuit board.

* * * * *

UNITED STATES PATENT AND TRADEMARK OFFICE
CERTIFICATE OF CORRECTION

PATENT NO. : 4,145,714
DATED : March 20, 1979

INVENTOR(S) : Robert W. MacDonald, Robert W. Yates

It is certified that error appears in the above-identified patent and that said Letters Patent are hereby corrected as shown below:

Abstract - Last Sentence

"from" should read -- about --.

Signed and Sealed this

Twenty-first Day of August 1979

[SEAL]

Attest:

Attesting Officer

LUTRELLE F. PARKER
Acting Commissioner of Patents and Trademarks